United States Patent
Ellington, Jr. et al.

(10) Patent No.: US 8,416,413 B2
(45) Date of Patent: Apr. 9, 2013

(54) PRODUCTS AND METHODS FOR IDENTIFYING ROCK SAMPLES

(76) Inventors: William Eugene Ellington, Jr., Houston, TX (US); Jacob Cecil Moore, Houston, TX (US); Mark Alan Smith, Houston, TX (US); Grigory Leonidovich Dubinsky, Houston, TX (US)

( * ) Notice: Subject to any disclaimer, the term of this patent is extended or adjusted under 35 U.S.C. 154(b) by 69 days.

(21) Appl. No.: 13/158,110

(22) Filed: Jun. 10, 2011

(65) Prior Publication Data

US 2012/0044498 A1    Feb. 23, 2012

Related U.S. Application Data

(60) Provisional application No. 61/401,934, filed on Aug. 23, 2010.

(51) Int. Cl.
*G01N 21/25* (2006.01)

(52) U.S. Cl.
USPC ........................................................ 356/406

(58) Field of Classification Search .................. 356/406
See application file for complete search history.

(56) References Cited

U.S. PATENT DOCUMENTS

| | | | |
|---|---|---|---|
| 4,624,367 A | 11/1986 | Shafer et al. | |
| 4,783,751 A | 11/1988 | Ehrlich et al. | |
| 4,868,883 A | 9/1989 | Chen | |
| 5,615,005 A * | 3/1997 | Valente et al. | 356/30 |
| 2002/0126328 A1 | 9/2002 | Lehmeier et al. | |
| 2006/0158652 A1 * | 7/2006 | Rooney et al. | 356/406 |
| 2009/0259446 A1 | 10/2009 | Zhang et al. | |
| 2009/0260415 A1 * | 10/2009 | Suarez-Rivera et al. | 73/7 |

OTHER PUBLICATIONS

Article 34 Amendment and Response; PCT/US11/39968; Products and Methods for Identifying Rock Samples; Feb. 16, 2012; 17 pages.
The International Search Report and the Written Opinion of the International Searching Authority; PCT/US11/39968; Oct. 26, 2011; 7 pages.
Kara E. Geisel, Written Opinion of the International Preliminary Examining Authority, International Application No. PCT/US11/39968, Oct. 22, 2012, 5 pages, International Preliminary Examining Authority, Alexandria, Virginia, US.

* cited by examiner

*Primary Examiner* — Kara E Geisel
(74) *Attorney, Agent, or Firm* — Crain, Caton & James

(57) ABSTRACT

Products and methods for identifying rock samples based on an average color value for each rock sample.

4 Claims, 4 Drawing Sheets

PRODUCTS AND METHODS FOR IDENTIFYING ROCK SAMPLES

CROSS-REFERENCE TO RELATED APPLICATIONS

The priority of U.S. Provisional Patent Application No. 61/401,934, filed on Aug. 23, 2010, is hereby claimed, and the specification thereof is incorporated herein by reference.

STATEMENT REGARDING FEDERALLY SPONSORED RESEARCH

Not applicable.

FIELD OF THE INVENTION

The present invention relates to products and methods for identifying rock samples. More particularly, the present invention relates to identifying rock samples based on an average color value for each rock sample.

BACKGROUND OF THE INVENTION

The crust of the Earth is composed of a great variety of igneous, metamorphic, and sedimentary rocks that generally sit in numerous distinctive layers. In order to understand this complex structure changes must be identified that distinguish one rock or mineral from another and to correlate them across wide lateral separation. Samples of layered rock are easily collected from vertical outcrops, either man-made (e.g., road cuts) or natural (e.g., mountainsides or valleys). When outcrops are not available or when the rocks are very deep, wells and cores provide access to samples of the rock not visible at the surface. Whether understanding the substrate for construction, environmental studies, water resources, mining, or oil and gas extraction, it is critical to recognize and understand the regional and local geology.

Numerous tools and techniques exist that provide information about rocks and minerals that might be encountered, ranging from direct chemical analysis to remote sensing of a multitude of physical rock parameters. Analyses of rock samples can be performed in an onsite or distant laboratory, or measurements can be taken remotely with tools lowered into holes or wells drilled into the rock or sediment. Some techniques are quite simple, and others are very expensive and complicated. For example, some tools and techniques measure different parameters, measure them using different methods or from different locations, analyze the measured data in different ways, and present the results of analysis in a variety of formats. Nevertheless, all of these tools and techniques work together to provide various properties and/or attributes of information that a trained person can use to identify, understand, and correlate specific rocks and minerals.

When describing a rock or mineral, not all of the information that a geologist might use is easily quantifiable. Geologic descriptions are commonly full of qualitative terminology and assessments. A geologist might use words such as "sandy," "shaley," "greenish," "gray," or "translucent" that may describe the grain size, texture, color, and so forth. The geologist might further qualify such descriptions with various modifiers—such as "light" or "dark," to better describe the specific way a rock sample appears to an observer. Whereas the human eye is good at seeing fine details and discriminating subtle distinctions of texture and color, the human brain is not good at converting these fine distinctions into language that can be easily and clearly understood by another person with the same level of detail as the observer's eye. In addition, the brain cannot retain an image with enough detail to unequivocally determine if one sample is identical to another sample previously observed. Even the use of color charts similar to those used to match paint samples is limited in precision and repeatability. Geologists therefore, are not always able to easily and/or accurately quantify information observed during the study of rocks and mineralogy.

SUMMARY OF THE INVENTION

The present invention overcomes one or more deficiencies in the prior art by providing products and methods for identifying rock samples based on an average color value for each rock sample.

In one embodiment, the present invention includes a method for identifying a rock sample, comprising: i) acquiring data from the rock sample; ii) determining an average color value for the rock sample; and iii) creating a well log based on average color values and a depth for each rock sample from a well.

Additional aspects, advantages and embodiments of the invention will become apparent to those skilled in the art from the following description of the various embodiments and related drawings.

BRIEF DESCRIPTION OF THE DRAWINGS

The patent application file contains at least one drawing executed in color. Copies of this patent application with color drawing(s) will be provided by the U.S. Patent and Trademark Office upon request and payment of the necessary fee.

The present invention is described below with references to the accompanying drawings in which like elements are referenced with like numerals and which.

DETAILED DESCRIPTION OF THE PREFERRED EMBODIMENTS

The subject matter of the present invention is described with specificity, however, the description itself is not intended to limit the scope of the invention. The subject matter thus, might also be embodied in other ways, to include different steps or combinations of steps similar to the ones described herein, in conjunction with other technologies. Moreover, although the term "step" may be used herein to describe different elements of methods employed, the term should not be interpreted as implying any particular order among or between various steps herein disclosed unless otherwise expressly limited by the description to a particular order. While the following description refers to the oil and gas industry, the systems and methods of the present invention are not limited thereto and may also be applied to other industries to achieve similar results.

In both ancient (cable-tool) and modern (rotary) drilling, rock is usually pulverized and subsequently removed from a hole or well bore. The exception is coring, a process of removing an intact cylinder of rock or sediment for preservation and later study. Nevertheless, the vast majority of rock available for study is in the form of "cuttings," the name most commonly used for the rock chips removed from a well being drilled. These cuttings were once removed with buckets or balers from holes and wells drilled using chiseling or percussion action to break and penetrate the rock at the bottom of the hole. Today, fluid or air forced through the annulus of a length of hollow drill pipe carry the cuttings, ground or broken away by the teeth of a rotary drill bit on the bottom end of the drill pipe, up to the surface through the annulus of the well between the wall of the well and the drill pipe. These cuttings are collected and sampled. The samples are bagged and labeled, making note of the depth from which a particular sample is associated. Samples are later analyzed in a variety of ways to look at mineralogy with X-ray diffraction and visual lithological description, at elemental abundance using X-ray fluorescence, and at the types and relative abundance of tiny microscopic fossils and pollens that are present in the sediment sampled.

Although the following method of analysis can be applied to core rock samples as well as to rock samples in the form of cuttings, the following description refers to cuttings since they are predominant source of material to be analyzed.

Figure 1:
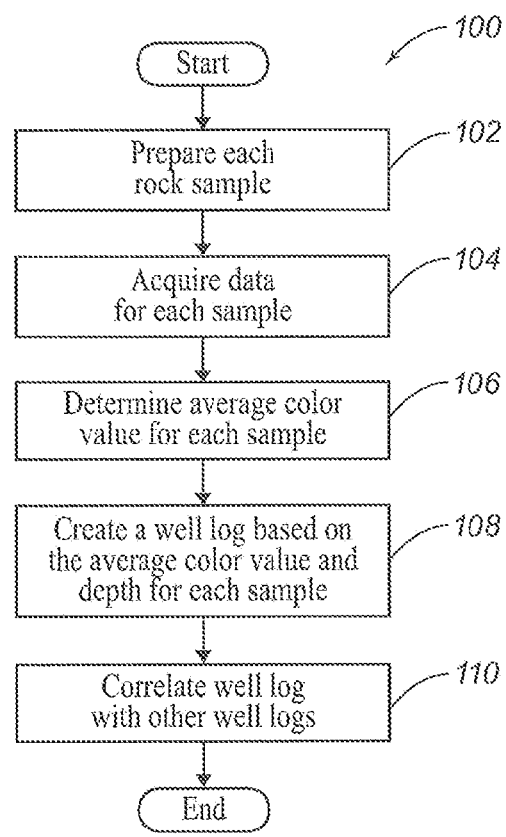
FIG. 1 is a flow diagram illustrating one embodiment of a method for implementing the present invention.

Referring now to FIG. 1, a flow diagram illustrates one embodiment of a method 100 for implementing the present invention.

In step 102, the rock sample (cuttings) is prepared using techniques well known in the art. The cuttings typically arrive in bags labeled with the well name and depths with which they are associated. Each bag is opened in turn, and a portion of the cuttings within that bag are removed and washed to remove drilling mud and additives which were circulated through the well bore during rotary drilling. The cuttings, rock chips broken away from the drilled rock formation, are sieved and retained as the drilling mud is washed away. The washing process involves differential application of a combination of water, detergents, heat (ovens), and mechanical separation. The precise order and combination of these depends upon a variety of factors, including the type of rock, its cementation and hardness, the type of drilling mud used, and the types of analyses planned for the rock sample. In addition, certain drilling additives may be particulate in nature and may not be easily separated from the cuttings during the washing process. This material can be manually separated and removed from the actual cuttings by a trained technician. Before analyses or before manual separation, the cuttings are dried, either in ovens or by evaporation, using fans at ambient temperatures.

Prior to the acquisition of data based on the cuttings, a portion of each sample may be placed into a small container (e.g. 90 m. paper cup) that is open at the top. Each sample is taken from a particular depth of the well being studied and is ready for the acquisition of data in step 104.

Alternatively, the cuttings may be prepared in the form of a liquid slurry before the acquisition of data in step 104. A sample of the cuttings is placed into a grinder or mortar with approximately 20-ml of distilled or DI (de-ionized) water. Care must be taken not to over-grind the sample. Hand grinding with mortar and pestle provides the greatest level of control. When the solid material is sufficiently ground, the particles will remain suspended in the liquid, creating a slurry. Each slurry may be placed into a 30-ml plastic cup.

It may also be more economical to combine the liquid slurry sample with other common techniques used to analyze and correlate cuttings and core material. A common form of study is the isolation, determination, and quantification of the microscopic fossils found in cuttings from sedimentary rock formations. An important group of these fossils has been classified by the obviously descriptive name "nannofossils" due to the tiny size (generally less than 30 microns) of them. Another alternative technique for preparing the rock sample therefore, may include creating slides with the liquid slurry that can be used by a paleontologist (biostratigrapher) and/or for data acquisition in step 104. Although any size may work, common laboratory glass slides measuring 75×25×1 mm are preferred. The glass slide is warmed to approximately 70 degrees Celsius. The liquid slurry is vigorously stirred with a clean glass rod for a few seconds. After standing undisturbed for about 45 seconds, a pipette or eyedropper is used to remove a portion of the liquid fraction containing the suspended solid cuttings. Several drops of this solution are placed on the warm glass slide and then smeared evenly across the surface of the slide. When the solution has dried, the slide is ready for step 104.

In step 104, data is acquired from the rock sample prepared in step 102 using a light source and photographic equipment or a spectrophotometer. The data is acquired by transmitting light at a rock sample and capturing transmitted, refracted and/or reflected light with photographic equipment or a spectrophotometer. The acquired data may also be referred to as spectral data, which may include data within and outside the visible spectrum. Rock samples in the form of cuttings, slurries, slides, etc. are organized and laid out in a regular pattern (preferably about 1 cm apart) on a flat surface of uniform color (preferably white). Although use of a spectrophotometer can capture data within and outside the visible spectrum, other photographic equipment may be used. In either case, the photographic equipment (e.g. digital camera) or a spectrophotometer is suspended above the group of samples, and one or more photographs are taken. In order to reduce any external variable factors, the same camera should be used with identical settings at a fixed distance (e.g. 80 cm.) from the flat surface to the focal point of the camera each time. The light source is also an important factor. It is best to use full spectrum light sources or bulbs, which may include, for example, a full spectrum fluorescent light source. Shadows can also be a problem. Therefore, using multiple sources and devices to reflect and "soften" the light give better results. At least two light sources may be used, which are physically separated from each other and reflected from special umbrellas used by professional photographers, to provide softer light with less glare and fewer shadows. These should be the only lights used during the acquisition of data (taking photographs). The room lights are turned off so that no extraneous light is reflected from the rock samples. If slurries are being analyzed, they should be stirred prior to data acquisition.

In step 106, an average color value is determined for each sample using the data acquired in step 104 and well known graphics programs such as, for example, Paint.NET®, which is publicly available freeware. The uncompressed raw data acquired in step 104 should be used. Because the images of multiple samples may be captured in a single photograph in step 104, each sample image is individually isolated and separately analyzed to determine the average color values.

Because graphics programs may alter values or compress files when attempting to save an image, a numerically-based color model is preferred. A color model is an abstract mathematical model describing the way colors can be represented as tuples (ordered lists of numbers used to describe other mathematical objects), typically as three or four values or color components. Commonly used color models are RGB (Red, Green, Blue), CMYK (Cyan, Magenta, Yellow, blacK), and HSV (Hue, Saturation, Value). Any color model may be used, however, the RGB model is illustrated in the following examples for its simplicity and familiarity. The RGB color model is an additive color model in which red, green, and blue light are added together in various ways to reproduce a broad array of colors. The main purpose of the RGB color model is for the sensing, representation, and display of images in electronic systems, such as televisions, computers, and digital photography. The color is expressed as an RGB triplet, and each component of the RGB triplet can vary from zero to a defined maximum value. If all of the components are at zero, the result is black. If all of the components are at a maximum value, the result is the brightest representable white.

The color values may be quantified and represented in several different ways, for example:

- From 0 to 1, with any fractional value in between. This representation is used in theoretical analyses, and in systems that use floating-point representations.
- Each color component value can also be written as a percentage, from 0% to 100%.
- In computing, the color component values are often stored as integer numbers in the range 0 to 255, the range that a single 8-bit byte can offer (by encoding 256 distinct values).
- High-end digital image equipment can deal with the integer range 0 to 65,535 for each primary color, by employing 16-bit words instead of 8-bit bytes.

Full intensity of the color component for red may therefore, be written in the different RGB notations illustrated in Table 1:

TABLE 1

| Representation | RGB triplet |
|---|---|
| Numerical | (1.0, 0.0, 0.0) |
| Percentage | (100%, 0%, 0%) |
| Digital 8-bit per | (255, 000, 000) |
| Digital 16-bit per | (65535, 0, 0) |

Figure 2A:
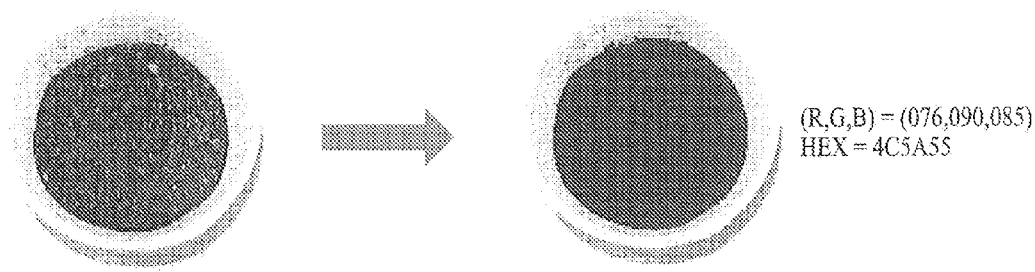
FIG. 2A illustrates an original image (photograph) of cuttings from a rock sample (left) compared to an "averaged" image and various quantifications representing average color values for the rock sample (right).
Figure 2B:
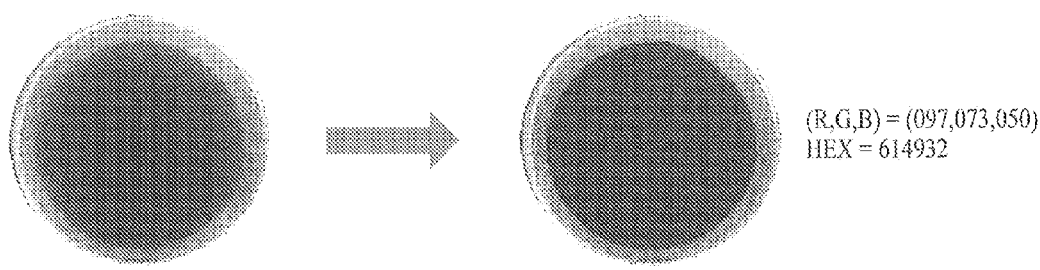
FIG. 2B illustrates an original image (photograph) of a liquid slurry containing cuttings from a rock sample (left) compared to an "averaged" image and various quantifications representing average color values for the rock sample (right).
Figure 2C:
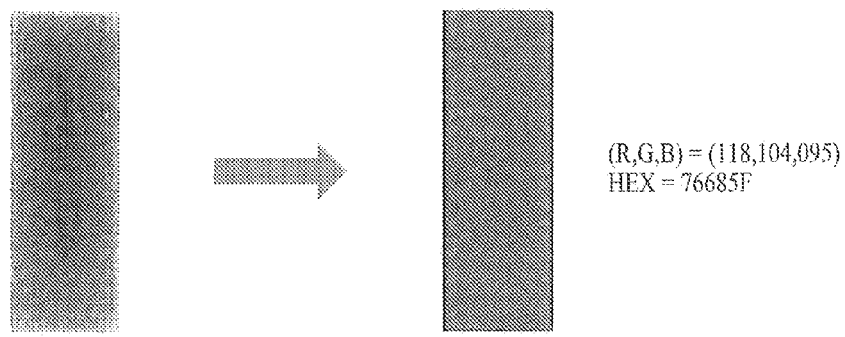
FIG. 2C illustrates an original image (photograph) of a slide containing a liquid slurry with cuttings from a rock sample (left) compared to an "averaged" image and various quantifications representing average color values for the rock sample (right).

In order to determine the average color value for a sample, the R-value, G-value, or B-value for each pixel is counted and the total R-values, G-values and B-values or divided by the total number of pixels. Preferably, the average color values for the sample are determined by counting the R-value, G-value and B-value for each pixel and dividing the total R-values, G-values and B-values by the total number of pixels. Each sample therefore, may have its own triplet of average RGB color values as illustrated in FIGS. 2A, 2B and 2C. In addition, ratios of the color value components often prove to be useful when uniquely identifying and correlating rock samples from different sources. Capturing the data for each sample at a higher resolution translates into a greater number of pixels and more accurate average RGB color values.

The individual color components of the average RGB color values can be represented in other formats through mathematical operations and transformations. For example, simple ratios of the individual (i.e., R/G) and multiple (i.e., R/(R+G+B)) average color components create additional representations of the average color values. Average color values from one color system (e.g., RGB) can also be converted to other color systems (e.g., CMYK or HSV) through mathematical transformations. It is also possible to transform the average RGB color values into i) a format easily recognized by computing applications for graphical display (e.g., hexadecimal format); and ii) an "averaged" image of the average RGB color values for the sample. In FIGS. 2A, 2B and 2C, for example, the original image is on the left and an "averaged" image is on the right. The uniform color of each "averaged" image is associated with a unique hexadecimal value that was created from the average RGB color values.

In step 108, a well log may be created based on the average color values and depth of each sample. The well log may be created in an Excel spreadsheet or other format using techniques well known in the art and/or conventional applications such as, for example, Oilfield Data Manager™, which is licensed by Senergy. Because the depth from which a sample was taken is a major factor in ordering the samples and correlating a group of samples from one well to a group taken from another well, it is convenient to place the data from step 106 in a well log format.

Figure 3:
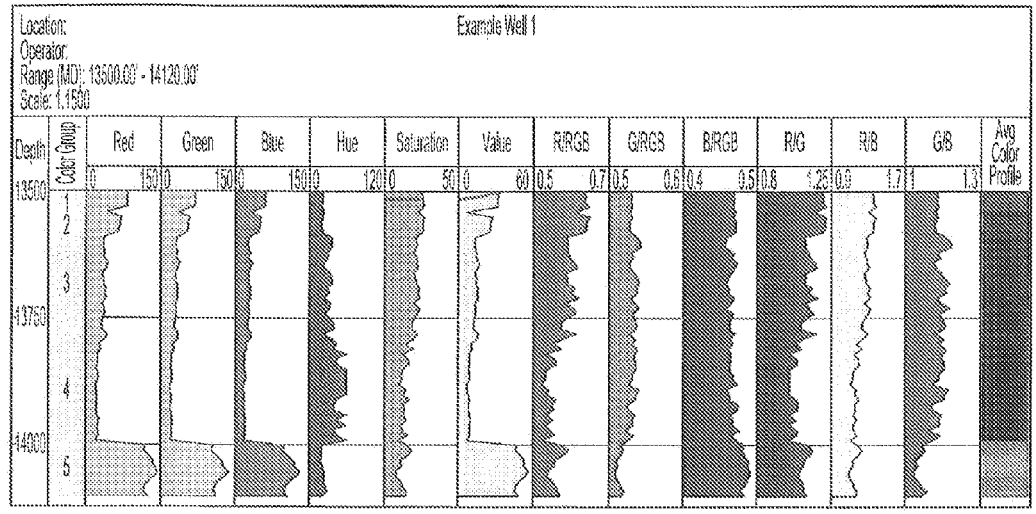
FIG. 3 is an exemplary well log illustrating the results of step 108 in FIG. 1.
Figure 4:
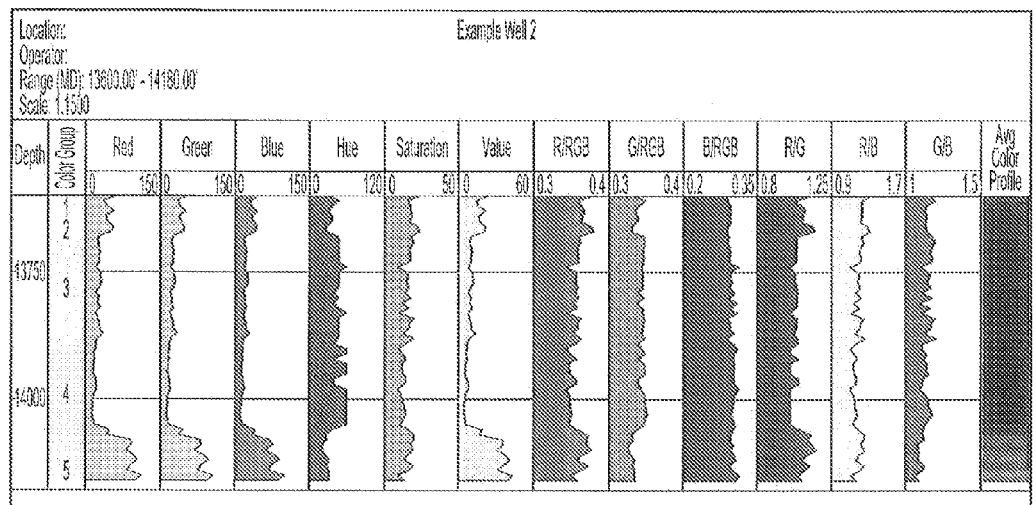
FIG. 4 is another exemplary well log illustrating the results of step 108 in FIG. 1.

In FIG. 3, an exemplary well log (well 1) illustrates the results of step 108. In FIG. 4, another exemplary well log (well 2) illustrates the results of step 108. In each exemplary well log, the data may be compiled with the sample depth laid out vertically and with horizontal scaling. The columns displayed in FIG. 3 and FIG. 4 can vary from numerical traces of color values to average color profiles based on the average color value(s) for each sample. Adding numerical traces of ratios can isolate and enhance relative differences between color value components for identification of color variation. Displaying the averaged image of the average color values for each sample in a vertical manner creates a color profile in the well log that intuitively represents what the colors of the rock strata might look like when looking down the wellbore. Any number of samples can be plotted in each well log, with the proximity of intervals limited only by the density of the sample cuttings or core. Changes in the average color value(s) with depth can be related to geologic variations within the sample.

Figure 5:
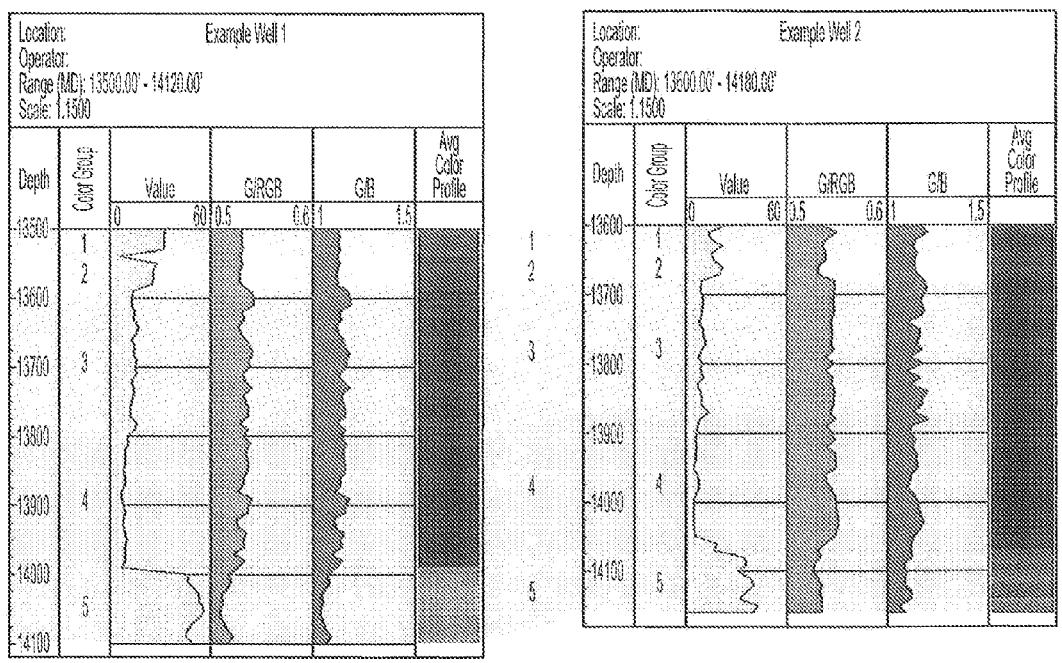
FIG. 5 is a comparison of exemplary well logs illustrating step 110 in FIG. 1.

In step 110, each well log created in step 108 may be correlated with another well log created in step 108 and/or created from another source. Referring now to FIG. 5, a comparison of exemplary well logs (well 1 and well 2) illustrates step 110. The comparison in FIG. 5 demonstrates how patterns of color in one well log correlate to the patterns of another well log. These correlations provide the geologist with key insights into the structure and stratigraphy of the area being studied.

The invention claimed is:

1. A method for indentifying a rock sample, comprising:
   acquiring data from the rock sample;
   determining an average color value for the rock sample; and
   creating a well log based on average color values and a depth for each rock sample from a well.

2. The method of claim 1, further comprising correlating the well log with another well log.

3. The method of claim 2, wherein the another well log is created based on average color values and a depth for each rock sample from another well.

4. The method of claim 3, wherein correlating the well log with the another well log includes comparing the average color values and the depth for each rock sample in the well log with the average color values and the depth for each rock sample in the another well log.

* * * * *